(12) United States Patent
Ahmed et al.

(10) Patent No.: US 8,503,712 B2
(45) Date of Patent: Aug. 6, 2013

(54) METHOD AND APPARATUS FOR DETERMINING BLOOD OXYGENATION USING A MOBILE COMMUNICATION DEVICE

(75) Inventors: Imtiaz Ahmed Ahmed, Glendale Heights, IL (US); Jasmin Farshi, Lake Forest, IL (US); Krishna Jonnalagadda, Mason, OH (US); Francesca Schuler, Des Plaines, IL (US)

(73) Assignee: Motorola Mobility LLC, Libertyville, IL (US)

( * ) Notice: Subject to any disclaimer, the term of this patent is extended or adjusted under 35 U.S.C. 154(b) by 1250 days.

(21) Appl. No.: 12/347,400

(22) Filed: Dec. 31, 2008

(65) Prior Publication Data
US 2010/0166252 A1  Jul. 1, 2010

(51) Int. Cl.
*G06K 9/00* (2006.01)

(52) U.S. Cl.
USPC .......................................... 382/100; 382/124

(58) Field of Classification Search
USPC .................................. 382/100, 124
See application file for complete search history.

(56) References Cited

U.S. PATENT DOCUMENTS

| | | | |
|---|---|---|---|
| 5,830,137 A * | 11/1998 | Scharf | 600/323 |
| 6,196,974 B1 * | 3/2001 | Miwa | 600/490 |
| 6,230,035 B1 | 5/2001 | Aoyagi et al. | |
| 6,775,565 B1 * | 8/2004 | Wieringa | 600/322 |
| 7,206,621 B2 | 4/2007 | Aoyagi et al. | |
| 7,751,594 B2 * | 7/2010 | Rowe et al. | 382/115 |
| 2002/0016533 A1 * | 2/2002 | Marchitto et al. | 600/310 |
| 2009/0028461 A1 * | 1/2009 | Wieringa et al. | 382/284 |

FOREIGN PATENT DOCUMENTS

WO  2006074307 A2  7/2006

OTHER PUBLICATIONS

Li, "Pulse Oximetry," 2007, SURJ2, pp. 11-15.*
Humphreys et al., "A CMOS Camera-Based Pulse Oximetry Imaging System," Sep. 1-4, 2005, IEEE, pp. 3493=3497.*
Mendelson et al., "A Mobile PDA-Based Wireless Pulse Oximeter," Jul. 19-21, 2005, Telehealth, pp. 1-6.*
G. Comtois and Y. Mendelson; Department of Biomedical Engineering, Worcestor Polytechnic Institute, Worcester, MA; A Wearable Wireless Reflectance Pulse Oximeter for Remote Triage Applications; IEEE 2006.

(Continued)

*Primary Examiner* — John Strege (57) ABSTRACT

A method (300) and apparatus (110) that determines blood oxygenation using a mobile communication device is disclosed. The method can include capturing (320) a plurality of images of skin using an array of pixels in a camera on a portable electronic device. The method can include comparing (330) image characteristics corresponding to the plurality of captured images at a first wavelength with image characteristics corresponding to the plurality of captured images at a second wavelength, the second wavelength being substantially distinct from the first wavelength. The method can include determining (340) blood oxygen level based on comparing the image characteristics.

21 Claims, 6 Drawing Sheets

OTHER PUBLICATIONS

John E. Scharf, MD & Stephen Athan, MS EE; University of South Florida Department of Anesthesiology, University of South Florida Center for Microelectronics Research; Direct Digital Capture of Pulse Oximetry Waveforms; IEEE 1993.

John E. Scharf, MD & Terry L. Rusch, BS EE; USF Department of Anesthesiology, USF Department of Electrical Engineering; Optimization of Portable Pulse Oximetry Through Fourier Analysis; IEEE 1993.

Yitzhak Mendelson, Vladimir Floroff, William Johnston and Paul Branche, Department of Biomedical Engineering and Bioengineering Institute, Worcester Polytechnic Institute, Worcester, MA; Telehealth Jul. 2005.

Micron Technology; Micron; 1/3-Inch CMOS Active-Pixel Digital Image Sensor; Mar. 2004.

Oximetry.ORG; Principles of Pulse Oximetry Technology; Sep. 10, 2002.

U.S. Appl. No. 12/043,515, filed Mar. 6, 2008.

* cited by examiner

METHOD AND APPARATUS FOR DETERMINING BLOOD OXYGENATION USING A MOBILE COMMUNICATION DEVICE

BACKGROUND

1. Field

The present disclosure is directed to a method and apparatus for determining blood oxygenation using a mobile communication device. More particularly, the present disclosure is directed to determining blood oxygenation from images captured using a camera on a portable electronic device.

2. Introduction

Presently, mobile communication device users can engage in active lifestyle activities and may desire to obtain corresponding heath metrics, such as their blood oxygen level. The ability to easily obtain key health metrics provides users with the ability to monitor their health and fitness. Tracking and monitoring data like distance, speed, caloric burn, heart rate, and other key measurements can help users achieve their health and fitness goals. For example, pulse oximeter sensors can be used to measure blood oxygen levels, such as $SpO_2$ as the percent of oxygen in blood for users with active lifestyles. Pulse oximeter sensors are also useful for patients with respiratory or cardiac issues and useful for athletes whose oxygen levels may decrease at high altitudes and/or with intense exercise. Most sensors require the use of Light Emitting Diode (LED) and infrared (IR) light sources and are not easy to integrate into existing mobile communication devices because such integration requires extensive hardware changes to the devices.

A pulse oximeter sensor can use red and infrared light to determine a heart rate for a user. As the user's heart pumps blood, a corresponding pulse distends blood-transporting capillaries, such as arteries and arterioles, in the subcutaneous tissue of the user. A corresponding change in volume can be detected by illuminating the skin with, for example, red and infrared light emitting diodes and then measuring the amount of light that is transmitted or reflected by use of a photodiode.

Unfortunately, present pulse oximeter sensors do not always meet all end user requirements in all application settings. At the very least, such devices require a user to maintain, keep powered, and carry about an additional device along with their other portable devices, such along with their cellular phone. This can lead to unwanted surprises regarding the unpowered status of the device during a time of need and/or the unavailability of the device during a time of need because the end user has not included the device amongst the items that the end user carries about. Furthermore, existing pulse oximeter sensors require additional hardware, such as an infrared light source and cannot be integrated within existing mobile communication devices without extensive hardware modifications.

Thus, there is a need for method and apparatus that determines blood oxygenation using a mobile communication device.

SUMMARY

A method and apparatus that determines blood oxygenation using a mobile communication device is disclosed. The method can include capturing a plurality of images of skin using an array of pixels in a camera on a portable electronic device. The method can include comparing image characteristics corresponding to the plurality of captured images at a first wavelength with image characteristics corresponding to the plurality of captured images at a second wavelength, the second wavelength being substantially distinct from the first wavelength. The method can include determining blood oxygen level based on comparing the image characteristics.

BRIEF DESCRIPTION OF THE DRAWINGS

In order to describe the manner in which advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Figure 1:
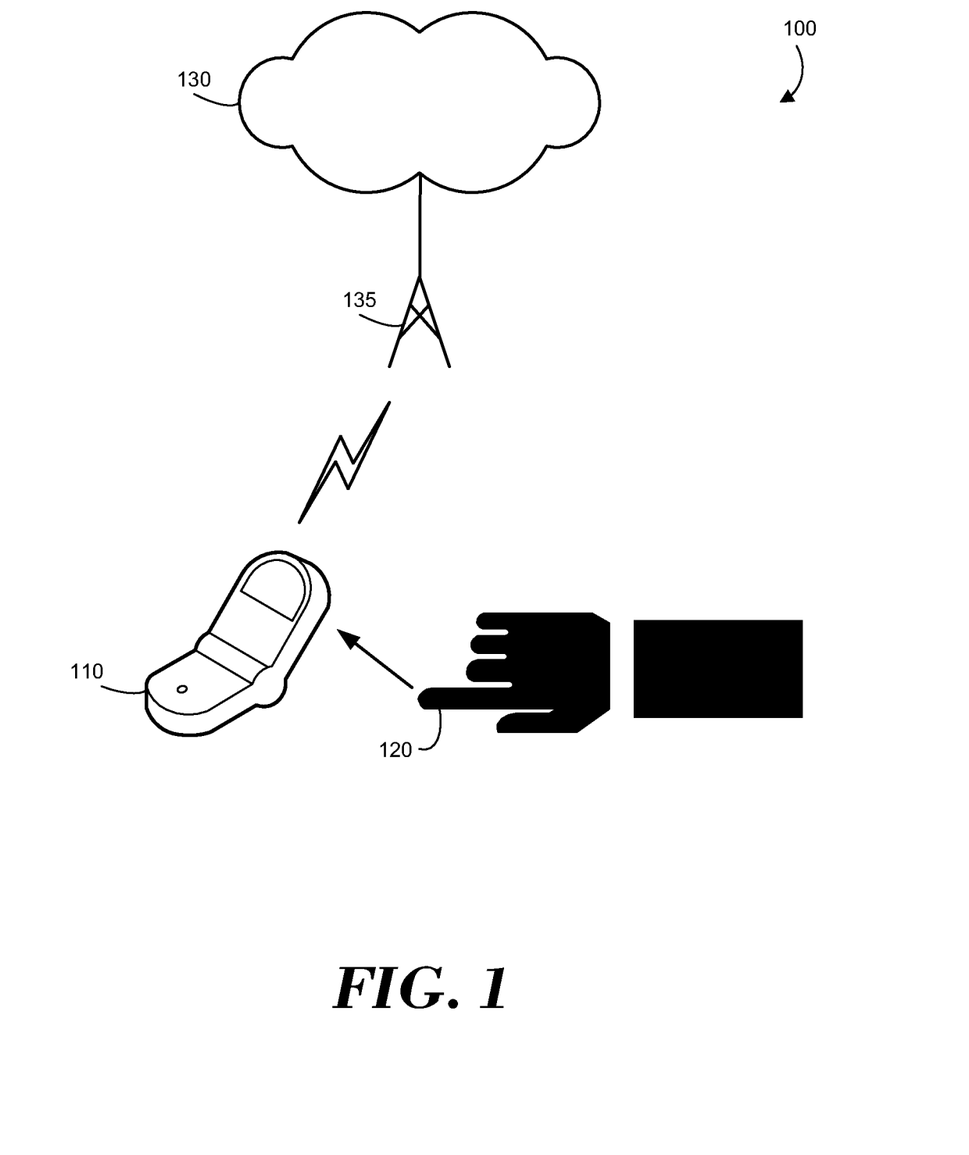
FIG. 1 illustrates an exemplary block diagram of a system in accordance with a possible embodiment.

FIG. 1 is an exemplary block diagram of a system 100 according to a possible embodiment. The system 100 can include a network 130, a terminal 110, and a base station 135. The terminal 110 may be a portable electronic device, such as a selective call receiver. For example, a selective call receiver can be mobile phone, a cellular phone, a personal digital assistant, a pager, or any other device that can engage in selective call receiver communications over a long distance wireless network 130. The base station 135 may be a cellular base station, a wireless local area network access point, or any other device that provides access between a wireless device and a network 130. The network 130 may include any type of network that is capable of sending and receiving signals, such as wireless signals. For example, the network 130 may include a wireless telecommunications network, a cellular telephone network, a Time Division Multiple Access (TDMA) network, a Code Division Multiple Access (CDMA) network, a satellite communications network, and other like communications systems. Furthermore, the network 130 may include more than one network and may include a plurality of different types of networks. Thus, the network 130 may include a plurality of data networks, a plurality of telecommunications networks, a combination of data and telecommunications networks and other like communication systems capable of sending and receiving communication signals.

In operation, a plurality of images of skin can be captured using an array of pixels in a camera on the terminal 110 to record the reflection of light through an anatomical extremity 120, such as a human finger. Image characteristics corresponding to the plurality of captured images at a first wavelength can be compared with image characteristics corresponding to the plurality of captured images at a second wavelength, where the second wavelength can be substantially distinct from the first wavelength. Blood oxygen level can be determined based on comparing the image characteristics.

For example, oxygen saturation of a subject can be determined using a camera, such as a conventional Complementary Metal-Oxide Semiconductor CMOS imager, available on a mobile device, such as the terminal 110. A user can place his/her finger in proximity to the camera and a video or picture sequence can be captured. Image analysis and signal processing techniques can then be used on the captured sequence to process and extract oxygen saturation (SpO$_2$). The processing can be done either in real-time, such as while the picture sequence is being captured, or can be done off-line after the picture sequence has been captured. An existing camera on the terminal 110 can be used for blood oxygen saturation and pulse rate measurement the process can be implemented in the terminal 110 without hardware changes. This feature can be implemented for users involved in fitness activities, those with special health care needs, heath care practitioners, and other users interested in determining oxygen saturation.

As a further example, a SpO$_2$ determination application can be launched in the terminal 110. The SpO$_2$ determination application can enable a video or picture mode on the terminal 110. A user can place their finger or other anatomical extremity in front of a camera on the terminal 110. The SpO$_2$ determination application can then determine the user's heart rate and SpO$_2$ levels of the user and can display the corresponding information on a display of the terminal 110. The SpO$_2$ determination application can also time stamp the corresponding data and store it on the terminal 110 or at a server coupled to the network 130.

As another example, SpO$_2$ can be determined according to:

$$SpO_2 = \frac{HbO_2 \text{ concentration}}{\text{Total haemoglobin concentration}} \equiv \frac{C_o}{C_o + C_r}$$

where SpO$_2$=oxygen saturation, C$_o$=oxyhaemoglobin concentration, and C$_r$=reduced haemoglobin concentration. According to Beer-Lambert's law for absorption of light through materials:

$$I_{out} = I_{in} \cdot 10^{-(\alpha_0 C_0 + \alpha_r C_r)l}$$

for light with wavelength λ and where I$_{in}$ is intensity of light passed through an artery of thickness l, I$_{out}$ is intensity of light exiting the artery, a$_o$ is the absorption coefficient of oxygenated blood (HbO$_2$) at wavelength λ, and α$_r$ is the absorption coefficient of deoxygenated blood (Hb) at wavelength λ. In order to solve for 2 variables, namely variables C$_o$ and C$_r$, a differential technique wherein 2 wavelengths of light can be used where:

$$I_1 = I_{in1} \cdot 10^{-(\alpha_{o1} C_0 + \alpha_{r1} C_r)l}$$

at wavelength λ$_1$, and $$I_2 = I_{in2} \cdot 10^{-(\alpha_{o2} C_0 + \alpha_{r2} C_r)l}$$

at wavelength λ$_2$. Thus, $$\frac{C_o}{C_o + C_r} = \frac{\alpha_{r2} R - \alpha_{r1}}{(\alpha_{r2} - \alpha_{o2})R - (\alpha_{r1} - \alpha_{o1})}$$

where:

$$R = \frac{\log_{10}(I_1/I_{in1})}{\log_{10}(I_2/I_{in2})}$$

The value of R can be calculated by measuring the voltages (V) at the output of photodiodes/pixels in the camera on the terminal 110:

$$R = \frac{\log_{10}((V_{ac} + V_{dc})/V_{dc}) \text{ for } \lambda_1}{\log_{10}((V_{ac} + V_{dc})/V_{dc}) \text{ for } \lambda_2}$$

which can be used to determine the oxygen saturation.

CMOS active pixel sensors, such as pixels in the camera of the terminal 110, can generally have a wider spectral response which leaks into the near infrared band. For example, the color blue can have a wavelength of 450-495 nm, the color green can have a wavelength of 495-570 nm, the color red can have a wavelength of 620-750 nm, and the near infrared band can have a wavelength of 750-950 nm. The pixel value of a given pixel at a given location in an array of pixels in the camera can be proportional to the current of the pixel:

$$\text{pixel value} \propto i_{x,y}(\lambda) \propto \iint_{\Delta t, \Delta \lambda} r_{x,y}(\lambda) \delta \lambda$$

where Δt is the exposure time setting of the camera, Δλ is the wavelength range sensitivity of the pixel because the corresponding imager can have a color filter on it, and i is the current generated at the pixel located at location x, y. Thus, the current generated by a pixel covered with a red, green, or blue color filter can depend on the spectral response of the color. The double integration over exposure time and wavelength range can be indicative of a pixel value being representative of electric charge being collected by the pixel over exposure time and over a range of wavelengths. Because it is not necessary to chose red and near infrared wavelengths to obtain an oxygen saturation value, other colors can be used, such as blue and red pixels, or other colors, to compute the R value in the equations above to eventually determine SpO$_2$:

$$R_{pure} = R - C$$

$$B_{pure} = B - C$$

where R$_{pure}$ is the pixel value of a red pixel without a spectral leakage component (C) and B$_{pure}$ is the pixel value of a blue pixel without a spectral leakage component (C). R$_{pure}$ and B$_{pure}$ can then be determined based on the spectral response of the sensor, which can also determine C, which can be subtracted from each of the red and blue pixels of the imager. Spatial and temporal information from camera video or picture images of an anatomical extremity can then be used to obtain heart rate information. For example, for SpO$_2$ determination, instead of using just images from the red color, other colors can be used, such as images from the blue color component. These colors can be used to obtain two sets of one-dimensional signals, such as one set corresponding to the red component and one set corresponding to the blue component. An alternating current (AC) value, such as V$_{AC}$ can be extracted for each of the red and blue or other wavelength (λ) components. The AC value can be extracted for the same point and time, such as in the same frame, for each wavelength component Also, multiple AC values can be extracted at different points in time and then averaged to average out any errors. The R value can be determined as follows:

$$R = \frac{\log_{10}((V_{ac}+V_{dc})/V_{dc}) \text{ for } \lambda_1}{\log_{10}((V_{ac}+V_{dc})/V_{dc}) \text{ for } \lambda_2}$$

$$= \frac{\log_{10}((V_{ac}/V_{dc}+1) \text{ for } \lambda_1}{\log_{10}((V_{ac}/V_{dc}+1) \text{ for } \lambda_2}$$

$$= \frac{(\log_{10}(V_{ac}) - \log 10(V_{dc})) \text{ for } \lambda_1}{(\log_{10}(V_{ac}) - \log 10(V_{dc})) \text{ for } \lambda_2}$$

$$\approx \frac{(\log_{10}(V_{ac})) \text{ for } \lambda_1}{(\log_{10}(V_{ac})) \text{ for } \lambda_2}$$

Since the Direct Current (DC) value for both wavelengths is approximately the same, and it is the ratio that we are interested in, it can be shown mathematically that the DC value can be ignored. Using the calculated R value, the $SpO_2$ value can be obtained using appropriate α values obtained from an absorption coefficient graph, table, or equation for red and blue or other colors.

Figure 2:
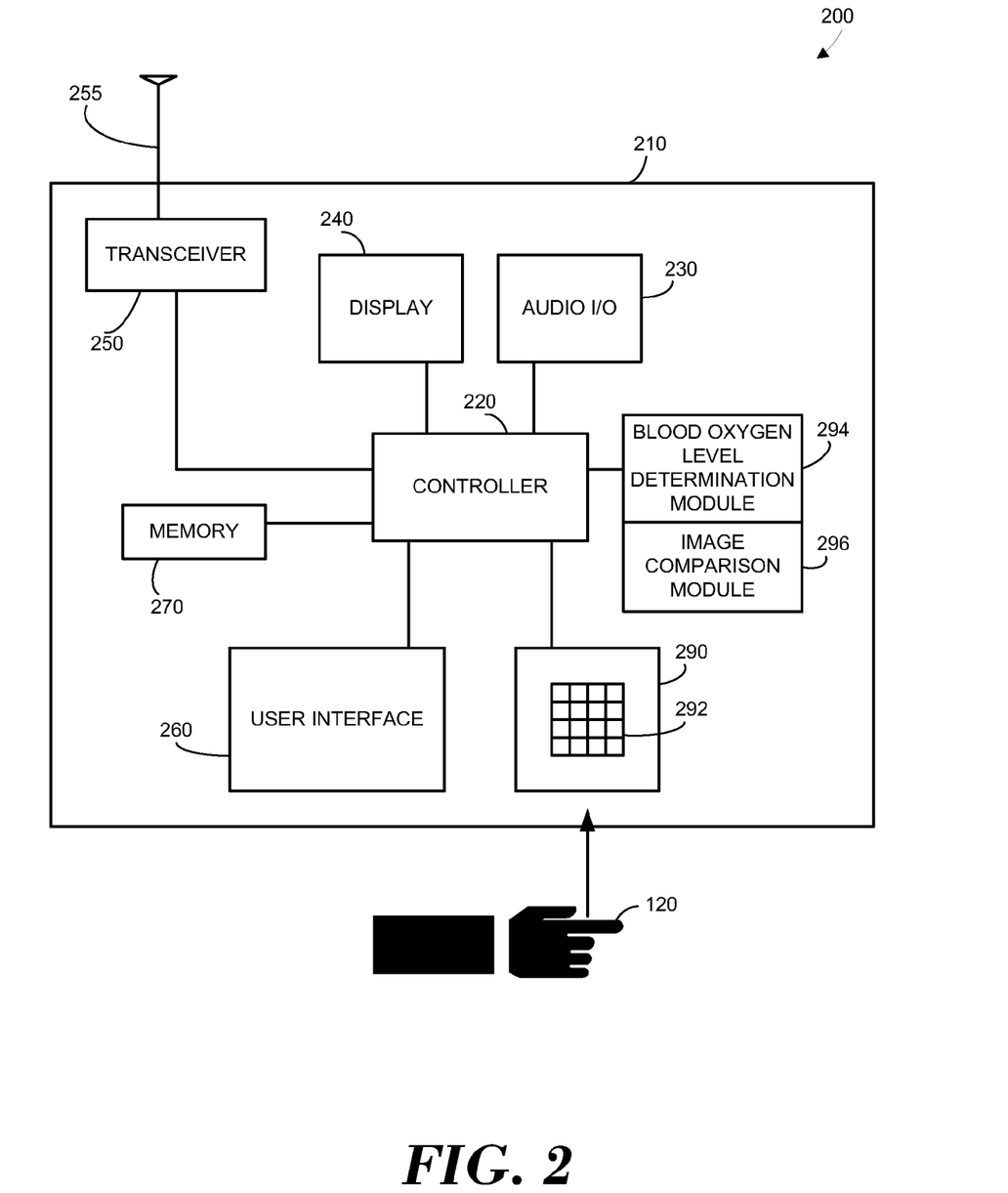
FIG. 2 illustrates an exemplary block diagram of an apparatus in accordance with a possible embodiment.

FIG. 2 is an exemplary block diagram of an apparatus 200, such as the terminal 110, according to a possible embodiment. The apparatus 200 can include a portable electronic device housing 210, a controller 220 coupled to the housing 210, audio input and output circuitry 230 coupled to the housing 210, a display 240 coupled to the housing 210, a selective call receiver transceiver 250 coupled to the housing 210, an antenna 255 coupled to the transceiver 250, a user interface 260 coupled to the housing 210, and a memory 270 coupled to the housing 210. The apparatus 200 can also include a camera 290 coupled to the housing 210, where the camera 290 can include an array of pixels 292. The camera 290 can be a complementary metal-oxide-semiconductor active pixel sensor digital imager camera or any other camera that can be coupled to a portable electronic device. The apparatus 200 can also include a blood oxygen level determination module 294 and an image comparison module 296. The blood oxygen level determination module 294 and the image comparison module 296 can be coupled to the controller 220, can reside within the controller 220, can reside within the memory 270, can be autonomous modules, can be software, can be hardware, or can be in any other format useful for a module on a apparatus 200.

The display 240 can be a liquid crystal display (LCD), a light emitting diode (LED) display, a plasma display, or any other means for displaying information. The transceiver 250 may include a transmitter and/or a receiver. The audio input and output circuitry 230 can include a microphone, a speaker, a transducer, or any other audio input and output circuitry. The user interface 260 can include a keypad, buttons, a touch pad, a joystick, an additional display, or any other device useful for providing an interface between a user and an electronic device. The memory 270 may include a random access memory, a read only memory, an optical memory, a subscriber identity module memory, or any other memory that can be coupled to a wireless communication device.

In operation, the selective call receiver transceiver 250 can be configured to engage in selective call receiver communications over a long distance wireless network, such as the network 130. The camera 290 can be configured to capture a plurality of images of skin 120 using the array of pixels 292. The controller 220 can be configured to control operations of the apparatus 200. The blood oxygen level determination module 294 can be configured to determine blood oxygen level based on the plurality of captured images.

The image comparison module 296 can be configured to compare image characteristics corresponding to the plurality of captured images at a first wavelength with image characteristics corresponding to the plurality of captured images at a second wavelength, where the second wavelength can be substantially distinct from the first wavelength. The blood oxygen level determination module 294 can be configured to determine blood oxygen level based on the compared image characteristics.

The image comparison module 296 can be configured to create a plurality of binary images from the plurality of captured images. The plurality of binary images can contain information corresponding to pixels exceeding a threshold. For example, the plurality of binary images can contain information corresponding to pixel data or pixel information exceeding a threshold. The image comparison module 296 can be configured to compare image characteristics corresponding to the plurality of binary images at the first wavelength with image characteristics corresponding to the plurality of binary images at the second wavelength.

The image comparison module 296 can also be configured to reduce dimensional content of the plurality of binary images by summing a number of pixels exceeding the threshold for each image of the plurality of binary images to generate reduced dimension information. The image comparison module can be configured to compare image characteristics corresponding to the reduced dimension information at the first wavelength with image characteristics corresponding to the reduced dimension information at the second wavelength.

The blood oxygen level can be based on:

$$\frac{(\log_{10}(V_{ac\lambda 1}))}{(\log_{10}(V_{ac\lambda 2}))}$$

where $V_{ac\lambda 1}$ can correspond to a pixel intensity value for the first wavelength obtained from the images from the camera 290 and where $V_{ac\lambda 2}$ can correspond to a pixel intensity value for the second wavelength obtained from the images from the camera 290.

The blood oxygen level can also be based on:

$$\frac{\alpha_{r2}R - \alpha_{r1}}{(\alpha_{r2} - \alpha_{o2})R - (\alpha_{r1} - \alpha_{o1})}$$

where $\alpha_{o1}$ can be an absorption coefficient of oxygenated blood for the first wavelength, where $\alpha_{o2}$ can be an absorption coefficient of oxygenated blood for the second wavelength, where $\alpha_{r1}$ can be an absorption coefficient of deoxygenated blood for the first wavelength, where $\alpha_{r2}$ can be an absorption coefficient of deoxygenated blood for the second wavelength, and where R can be a ratio based on the absorbance of light at the first wavelength to the absorbance of light at the second wavelength.

Figure 3:
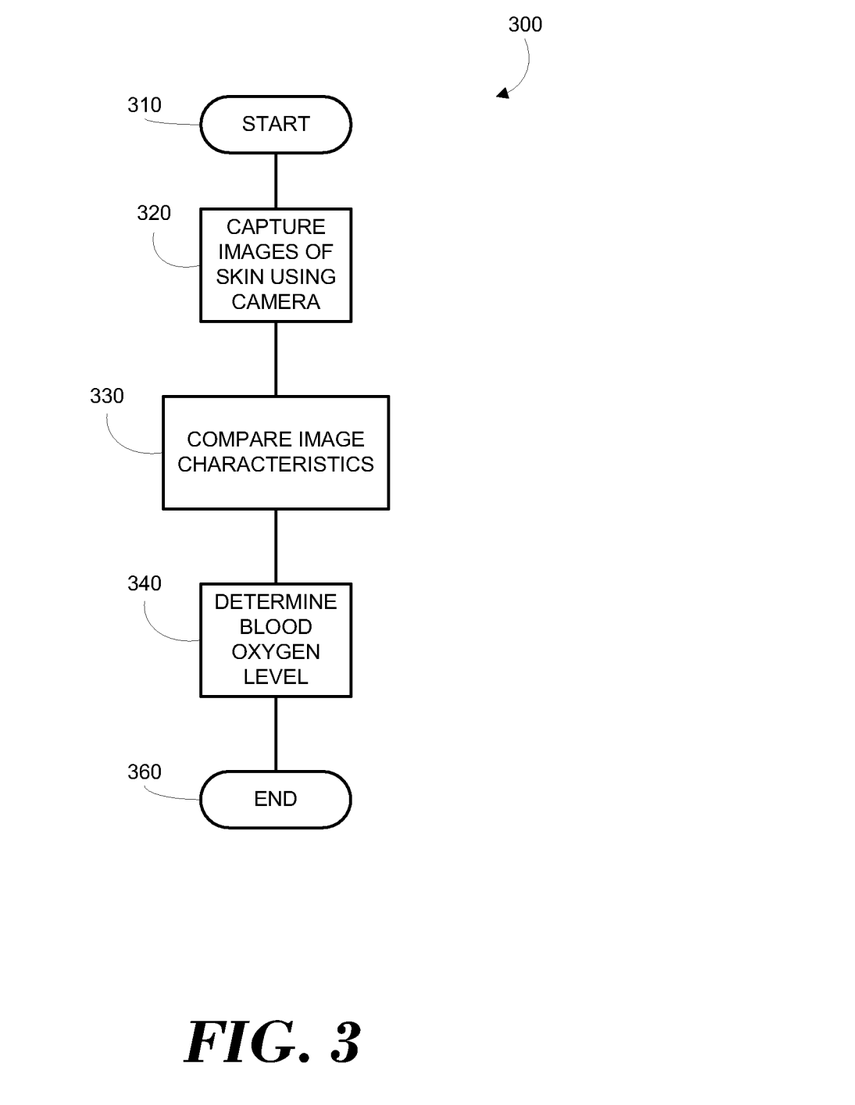
FIG. 3 is an exemplary flowchart illustrating the operation of an apparatus in accordance with a possible embodiment.
Figure 5:
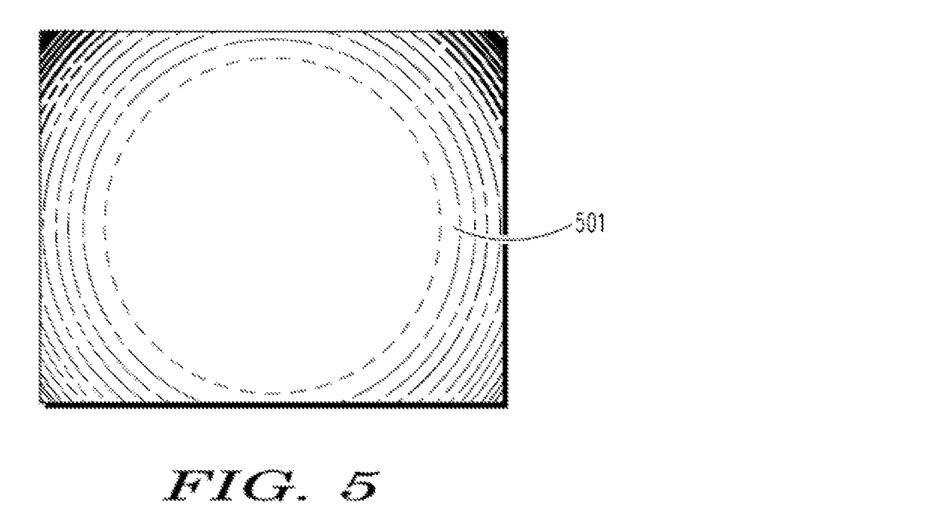
FIG. 5 is an illustrative example of a visible light image in accordance with a possible embodiment.

FIG. 3 is an exemplary flowchart 300 illustrating the operation of the apparatus 200 according to a possible embodiment. At 310, the flowchart begins. At 320, a plurality of images of skin can be captured using an array of pixels in a camera on a portable electronic device. Pixels can be sensor elements, sensels, pixel sensors, or any other pixels that can be used in an array in a camera. For example, a plurality of images of skin can be captured by using an array of pixels in a camera to record the reflection of light through a human anatomical extremity. The plurality of images of skin can be captured by illuminating skin using a portable electronic device light emitting diode light source on the same side of the portable electronic device as the camera and the plurality of images of the illuminated skin can be captured using an array of pixels in the camera on the portable electronic device. The plurality of images of skin can also be captured without using a dedicated infrared light source. For example, a dedicated infrared light source can be a light source dedicated to illuminating skin with infrared light for determining blood oxygen levels and such a light source is not necessary for the method. The plurality of images of skin can also be captured without using any dedicated light source. For example, the plurality of images of skin can be captured with the camera using ambient light. Also, the plurality of images of skin can be captured while the camera is pressed against the skin. FIG. 5 illustrates an example of a visible light image 501 that can be captured using an array of pixels in a camera on a portable electronic device.

At 330, image characteristics corresponding to the plurality of captured images at a first wavelength can be compared with image characteristics corresponding to the plurality of captured images at a second wavelength, where the second wavelength can be substantially distinct from the first wavelength. For example, a raw Bayer image can be decomposed into Red Green and Blue (RGB) sub-images from the constituent RGB Bayer pixel data. The sub-images can represent or correspond to the plurality of captured images at different wavelengths. At 340, blood oxygen level can be determined based on comparing the image characteristics. The blood oxygen level and heart rate information can then be displayed on a display on a portable electronic device. The blood oxygen level and heart rate information can also be stored on the portable electronic device and/or transmitted to and stored on a server remote from the portable electronic device.

The blood oxygen level can be based on:

$$\frac{(\log_{10}(V_{ac\lambda 1}))}{(\log_{10}(V_{ac\lambda 2}))}$$

where $V_{ac\lambda 1}$ can correspond to a pixel intensity value for the first wavelength obtained from the images from the camera and where $V_{ac\lambda 2}$ can correspond to a pixel intensity value for the second wavelength obtained from the images from the camera. For example, $V_{ac\lambda 1}$ can be based on current, voltage, pixel intensity, or other indicia and can be based on a sum of pixels exceeding a threshold in one image corresponding to wavelength $\lambda_1$.

The blood oxygen level can be based on:

$$\frac{\alpha_{r2} R - \alpha_{r1}}{(\alpha_{r2} - \alpha_{o2})R - (\alpha_{r1} - \alpha_{o1})}$$

where $\alpha_{o1}$ can be an absorption coefficient of oxygenated blood for the first wavelength, where $\alpha_{o2}$ can be an absorption coefficient of oxygenated blood for the second wavelength, where $\alpha_{r1}$ can be an absorption coefficient of deoxygenated blood for the first wavelength, where $\alpha_{r2}$ can be an absorption coefficient of deoxygenated blood for the second wavelength, and where R can be a ratio based on the absorbance of light at the first wavelength to the absorbance of light at the second wavelength. For example, the $\alpha$ values can be obtained from curves that are predetermined and calibrated for the camera or imager that is being used. The curves can be based on absorption coefficients vs. wavelength.

R can be based on:

$$R = \frac{(\log_{10}(V_{ac\lambda 1}))}{(\log_{10}(V_{ac\lambda 2}))}$$

where $V_{ac\lambda 1}$ can correspond to a pixel intensity value for the first wavelength $\lambda_1$ obtained from the images from the camera and where $V_{ac\lambda 2}$ can correspond to a pixel intensity value for the second wavelength $\lambda_2$ obtained from the images from the camera. At 350, the flowchart 300 ends.

Figure 4:
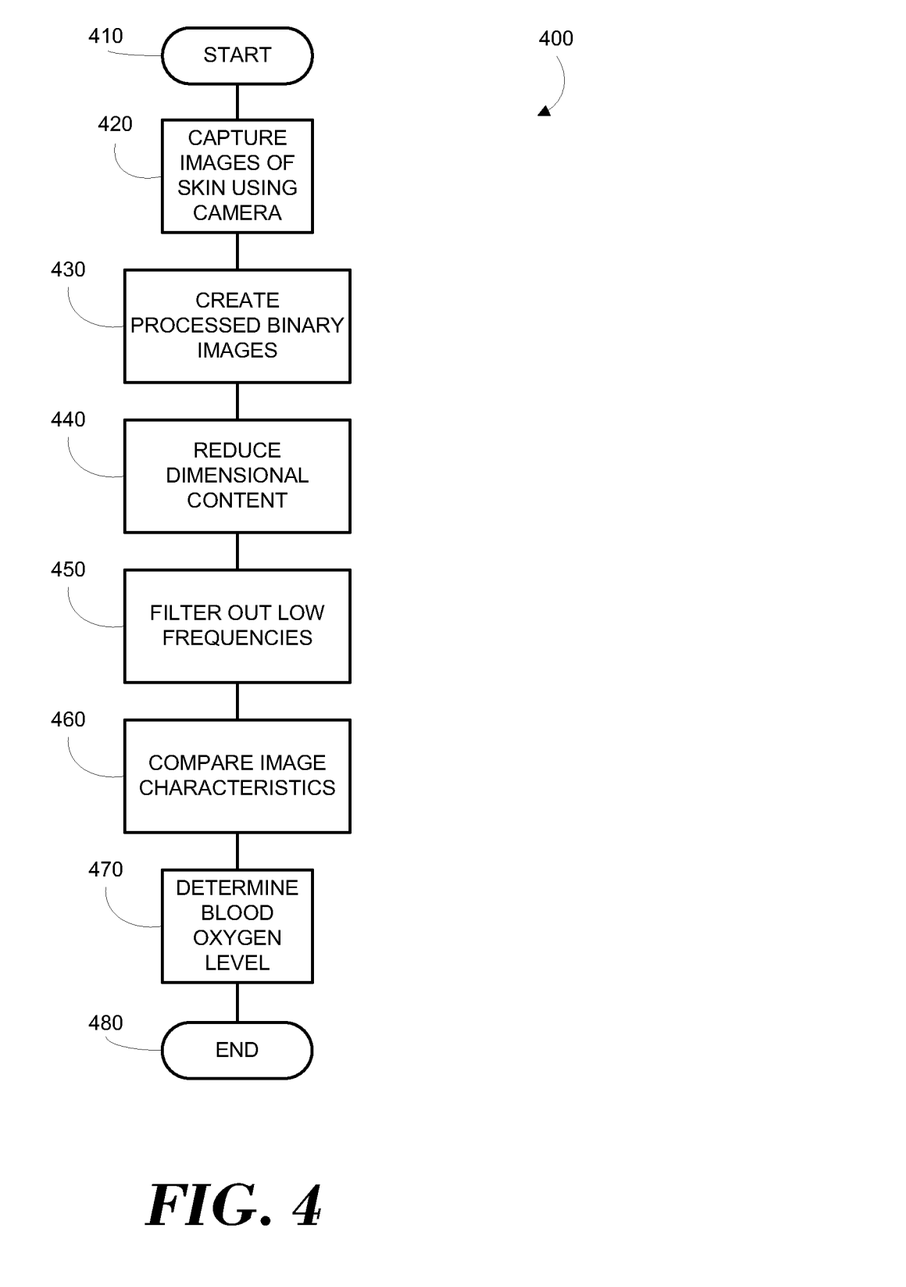
FIG. 4 is an exemplary flowchart illustrating the operation of an apparatus in accordance with a possible embodiment.
Figure 6:
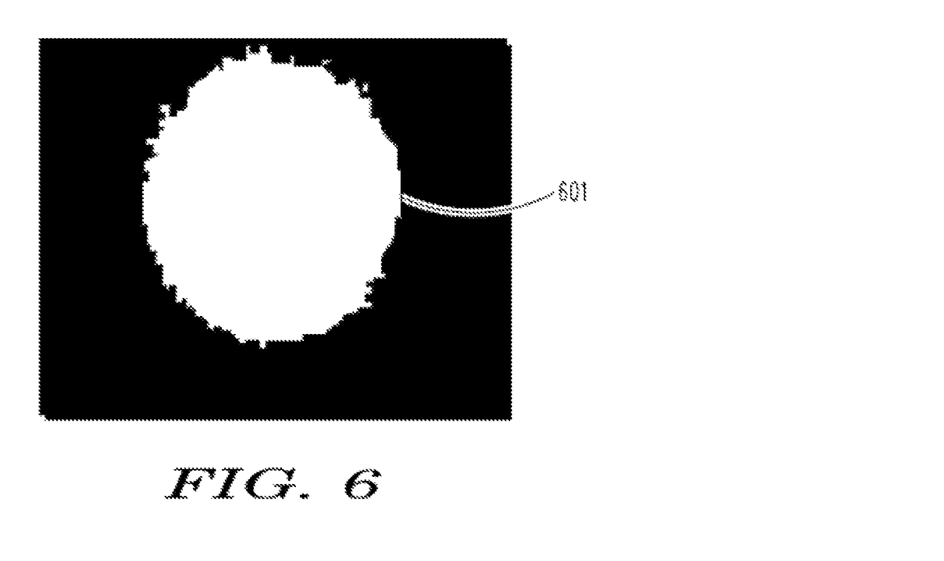
FIG. 6 is an illustrative example of a resultant binary image in accordance with a possible embodiment.

FIG. 4 is an exemplary flowchart 400 illustrating the operation of the apparatus 200 according to a possible embodiment. The flowchart 400 can incorporate features of corresponding elements from the flowchart 300. At 410, the flowchart begins. At 420, a plurality of images of skin can be captured using an array of pixels in a camera on a portable electronic device. For example, the plurality of images of skin can be captured while the camera is pressed against the skin. The captured images can be colored images which can be represented in raw Bayer Red Green and Blue (RGB) values. At 430, a plurality of binary images can be created based on the plurality of captured images, where the plurality of binary images can contain information corresponding to pixels exceeding a threshold. For example, the plurality of binary images can be created by processing the plurality of captured images, can be created from decomposed sub-images, can be created from a plurality of captured and decomposed images, or can otherwise be based on the plurality of captured images. As a further example, creating a plurality of binary images can include extracting a raw Bayer image that can be decomposed into RGB sub-images from constituent RGB Bayer pixel data. FIG. 6 illustrates an example of one of the plurality of binary images 601.

Figure 7:
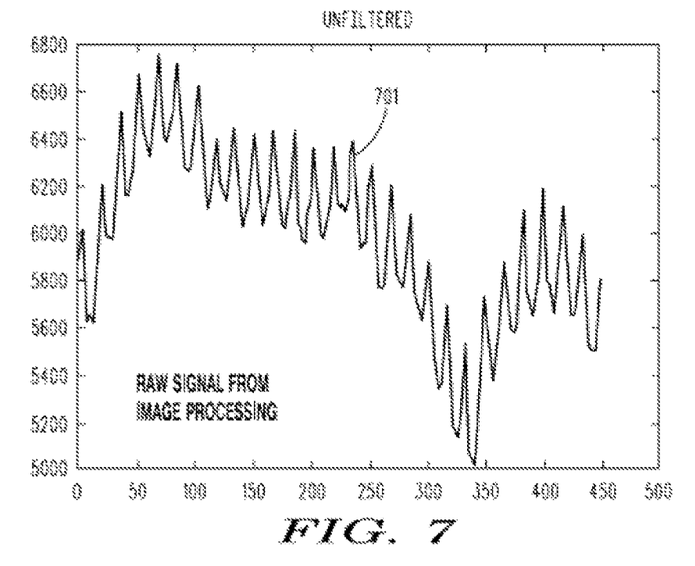
FIG. 7 is a reduced dimensionality graphic representation corresponding to the resultant binary image in accordance with a possible embodiment.

At 440, dimensional content of the plurality of binary images can be reduced to generate reduced dimension information. The dimensional content of the plurality of binary images can be reduced by summing a number of pixels exceeding the threshold for each image of the binary images to generate reduced dimension information. For example, the threshold can be used to convert individual sub-images into corresponding binary images. The dimensionality reduction can be due to summing of binarized pixel values for each of the sub-images, hence giving the area. FIG. 7 illustrates an example reduced dimensionality graphic representation 701 corresponding to the binary image 601.

Figure 8:
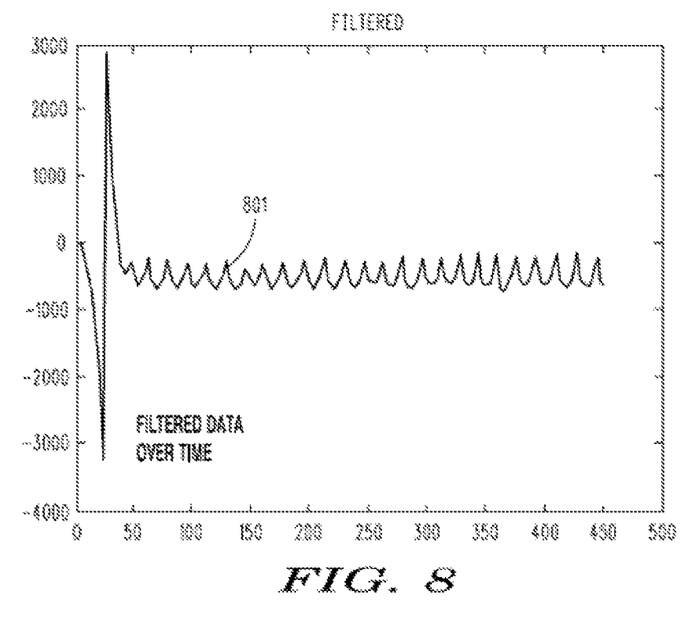
FIG. 8 is a filtered reduced dimensionality graphic representation corresponding to the resultant binary image in accordance with a possible embodiment.

At 450, low frequencies of the reduced dimension information can be filtered out to generate filtered reduced dimension information. FIG. 8 illustrates an example filtered reduced dimensionality graphic representation 801 corresponding to the binary image 601. At 460, image characteristics corresponding to the filtered reduced dimension information at the first wavelength can be compared with image characteristics corresponding to the filtered reduced dimension information at the second wavelength. At 470 blood oxygen level can be determined based on comparing the image characteristics. At 480, the flowchart 400 ends.

According to a related embodiment, at 420, a plurality of images of skin can be captured using an array of pixels in a camera on a selective call receiver device. The selective call receiver device can be configured to engage in selective call receiver communications over a long distance wireless network. At 430, a plurality of binary images can be created from the plurality of captured images. The plurality of binary images can contain information corresponding to pixels of the plurality of captured images exceeding a threshold. At 460, image characteristics corresponding to the plurality of binary images at the first wavelength can be compared with image characteristics corresponding to the plurality of binary images at the second wavelength. The second wavelength can be substantially distinct from the first wavelength. At 470, blood oxygen level can be determined based on comparing the image characteristics. At 480, the flowchart 400 ends.

Embodiments can provide for a scheme that measures $SpO_2$ level via a mobile phone camera. The scheme can work in the visible light spectrum with object being illuminated with background light through a finger or with a camera flash reflecting off a finger. A camera can be used in the visible spectrum to capture series of images and extract blood oxygen levels can be extracted from the images by comparing light absorption and image characteristics of a two-dimensional image at two distinct visible wavelengths. An infrared light source or a dedicated light source is not necessary for measuring $SpO_2$ levels.

The methods of this disclosure are preferably implemented on a programmed processor. However, the operations of the embodiments may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the operations of the embodiments may be used to implement the processor functions of this disclosure.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be enabled to make and use the teachings of the disclosure by simply employing the elements of the independent claims. Accordingly, the preferred embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. Also, relational terms, such as "top," "bottom," "front," "back," "horizontal," "vertical," and the like may be used solely to distinguish a spatial orientation of elements relative to each other and without necessarily implying a spatial orientation relative to any other physical coordinate system. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising."

We claim:

1. A method comprising:

capturing a plurality of images of skin using an array of pixels in a camera on a portable electronic device;

comparing image characteristics corresponding to the plurality of captured images at a first wavelength with image characteristics corresponding to the plurality of captured images at a second wavelength, the second wavelength being substantially distinct from the first wavelength; and determining blood oxygen level based on comparing the image characteristics, wherein the first wavelength is a first wavelength of visible light and wherein the second wavelength is a second wavelength of visible light.

2. The method according to claim 1, further comprising creating a plurality of binary images based on the plurality of captured images, where the plurality of binary images contain information corresponding to pixels exceeding a threshold, wherein comparing image characteristics comprises comparing image characteristics corresponding to the plurality of binary images at the first wavelength with image characteristics corresponding to the plurality of binary images at the second wavelength.

3. The method according to claim 2, wherein creating a plurality of binary images includes extracting raw Bayer images based on the plurality of captured images.

4. The method according to claim 2, further comprising reducing dimensional content of the plurality of binary images to generate reduced dimension information, wherein comparing image characteristics comprises comparing image characteristics corresponding to the reduced dimension information at the first wavelength with image characteristics corresponding to the reduced dimension information at the second wavelength.

5. The method according to claim 4, wherein reducing the dimensional content of the plurality of binary images comprises summing a number of pixels exceeding the threshold for each image of the plurality of binary images to generate reduced dimension information.

6. The method according to claim 4, further comprising filtering out low frequencies of the reduced dimension information to generate filtered reduced dimension information, wherein comparing image characteristics comprises comparing image characteristics corresponding to the filtered reduced dimension information at the first wavelength with image characteristics corresponding to the filtered reduced dimension information at the second wavelength.

7. The method according to claim 1, wherein the blood oxygen level is based on:

$$\frac{(\log_{10}(V_{ac\lambda 1}))}{(\log_{10}(V_{ac\lambda 2}))}$$

where $V_{ac\lambda 1}$ corresponds to a pixel intensity value for the first wavelength obtained from the images from the camera, and where $V_{ac\lambda 2}$ corresponds to a pixel intensity value for the second wavelength obtained from the images from the camera.

8. The method according to claim 1, wherein the blood oxygen level is based on:

$$\frac{\alpha_{r2}R - \alpha_{r1}}{(\alpha_{r2} - \alpha_{o2})R - (\alpha_{r1} - \alpha_{o1})}$$

where $\alpha_{o1}$ is an absorption coefficient of oxygenated blood for the first wavelength,
where $\alpha_{o2}$ is an absorption coefficient of oxygenated blood for the second wavelength,
where $\alpha_{r1}$ is an absorption coefficient of deoxygenated blood for the first wavelength,
where $\alpha_{r2}$ is an absorption coefficient of deoxygenated blood for the second wavelength, and
where R is a ratio based on the absorbance of light at the first wavelength to the absorbance of light at the second wavelength.

9. The method according to claim 8, where:

$$R = \frac{(\log_{10}(V_{ac\lambda 1}))}{(\log_{10}(V_{ac\lambda 2}))}$$

where $V_{ac\lambda 1}$ corresponds to a pixel intensity value for the first wavelength obtained from the images from the camera, and
where $V_{ac\lambda 2}$ corresponds to a pixel intensity value for the second wavelength obtained from the images from the camera.

10. The method according to claim 1, wherein the portable electronic device comprises a selective call receiver.

11. The method according to claim 1, further comprising illuminating skin using a portable electronic device light emitting diode light source on the same side of the portable electronic device as the camera,
wherein capturing comprises capturing a plurality of images of the illuminated skin using an array of pixels in the camera on the portable electronic device.

12. The method according to claim 1, wherein the camera comprises a complementary metal-oxide-semiconductor active pixel sensor digital imager camera.

13. The method according to claim 1, wherein blood oxygen level is determined without using a dedicated infrared light source.

14. An apparatus comprising:
a portable electronic device housing;
a selective call receiver transceiver coupled to the portable electronic device housing, the selective call receiver transceiver configured to engage in selective call receiver communications over a long distance wireless network;
a camera coupled to the portable electronic device housing, the camera including an array of pixels, the camera configured to capture a plurality of images of skin using the array of pixels;
a controller coupled to the camera, the controller configured to control operations of the apparatus; and
a blood oxygen level determination module coupled to the controller, the blood oxygen level determination module configured to compare image characteristics corresponding to the plurality of captured images at a first wavelength of visible light with image characteristics corresponding to the plurality of captured images at a second wavelength of visible light, the second wavelength being distinct from the first wavelength, and the blood oxygen level determination module configured to determine blood oxygen level based on comparing the image characteristics.

15. The apparatus according to claim 14, further comprising an image comparison module coupled to the controller, the image comparison module configured to compare image characteristics corresponding to the plurality of captured images at a first wavelength with image characteristics corresponding to the plurality of captured images at a second wavelength, the second wavelength being substantially distinct from the first wavelength,
wherein the blood oxygen level determination module is configured to determine blood oxygen level based on the compared the image characteristics.

16. The apparatus according to claim 15,
wherein the image comparison module is configured to create a plurality of binary images from the plurality of captured images, where the plurality of binary images contain information corresponding to pixels exceeding a threshold, and
wherein the image comparison module is configured to compare image characteristics by comparing image characteristics corresponding to the plurality of binary images at the first wavelength with image characteristics corresponding to the plurality of binary images at the second wavelength.

17. The apparatus according to claim 16, wherein the image comparison module is configured to reduce dimensional content of the plurality of binary images by summing a number of pixels exceeding the threshold for each image of the plurality of binary images to generate reduced dimension information,
wherein the image comparison module is configured to compare image characteristics by comparing image characteristics corresponding to the reduced dimension information at the first wavelength with image characteristics corresponding to the reduced dimension information at the second wavelength.

18. The apparatus according to claim 14, wherein the blood oxygen level is based on:

$$\frac{(\log_{10}(V_{ac\lambda 1}))}{(\log_{10}(V_{ac\lambda 2}))}$$

where $V_{ac\lambda 1}$ corresponds to a pixel intensity value for the first wavelength obtained from the images from the camera, and
where $V_{ac\lambda 2}$ corresponds to a pixel intensity value for the second wavelength obtained from the images from the camera.

19. The apparatus according to claim 14, wherein the blood oxygen level is based on:

$$\frac{\alpha_{r2}R - \alpha_{r1}}{(\alpha_{r2} - \alpha_{o2})R - (\alpha_{r1} - \alpha_{o1})}$$

where $\alpha_{o1}$ is an absorption coefficient of oxygenated blood for the first wavelength,
where $\alpha_{o2}$ is an absorption coefficient of oxygenated blood for the second wavelength,
where $\alpha_{r1}$ is an absorption coefficient of deoxygenated blood for the first wavelength,
where $\alpha_{r2}$ is an absorption coefficient of deoxygenated blood for the second wavelength, and where R is a ratio based on the absorbance of light at the first wavelength to the absorbance of light at the second wavelength.

20. A method comprising:

capturing a plurality of images of skin using an array of pixels in a camera on a selective call receiver device, the selective call receiver device configured to engage in selective call receiver communications over a long distance wireless network;

creating a plurality of binary images from the plurality of captured images, where the plurality of binary images contain information corresponding to pixels of the plurality of captured images exceeding a threshold;

comparing image characteristics corresponding to the plurality of binary images at a first wavelength with image characteristics corresponding to the plurality of binary images at a second wavelength, the second wavelength being substantially distinct from the first wavelength, where the first wavelength is a first wavelength of visible light and where the second wavelength is a second wavelength of visible light; and determining blood oxygen level based on comparing the image characteristics.

21. The method according to claim 1, wherein capturing comprises reflectively capturing a plurality of images of skin using an array of pixels in a camera on a portable electronic device.

* * * * *